(12) United States Patent
Bowman et al.

(10) Patent No.: US 10,012,601 B2
(45) Date of Patent: *Jul. 3, 2018

(54) NONAQUEOUS RADIOPAQUE FLUID AND ASSOCIATED IMAGING SYSTEM AND METHOD

(71) Applicant: The Boeing Company, Chicago, IL (US)

(72) Inventors: Elizabeth M. Bowman, Madison, AL (US); Danielle N. Bowman, Harvest, AL (US); Dennis L. Coad, Madison, AL (US); Alan Buitekant, Huntsville, AL (US); Chris T. Radcliffe, Harvest, AL (US)

(73) Assignee: The Boeing Company, Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/591,753

(22) Filed: May 10, 2017

(65) Prior Publication Data

US 2017/0248531 A1    Aug. 31, 2017

Related U.S. Application Data

(63) Continuation of application No. 14/478,241, filed on Sep. 5, 2014.

(51) Int. Cl.
*G01N 23/18* (2018.01)
*G01N 23/04* (2018.01)

(52) U.S. Cl.
CPC ............. *G01N 23/04* (2013.01); *G01N 23/18* (2013.01); *G01N 2223/319* (2013.01); *G01N 2223/404* (2013.01); *G01N 2223/646* (2013.01)

(58) Field of Classification Search
None
See application file for complete search history.

(56) References Cited

U.S. PATENT DOCUMENTS 9,678,022 B2 *   6/2017   Bowman ............... G01N 23/18
2016/0361950 A1 * 12/2016  Shaughnessy ......... B60C 9/005

* cited by examiner

*Primary Examiner* — Thomas R Artman
(74) *Attorney, Agent, or Firm* — Walters & Wasylyna LLC

(57) ABSTRACT

An imaging system including an imaging device having a field of view and a nonaqueous radiopaque fluid positionable in the field of view, the nonaqueous radiopaque fluid having a radiodensity that is between that of a metallic portion and a non-metallic portion of an object to be imaged by the imaging device.

20 Claims, 4 Drawing Sheets

NONAQUEOUS RADIOPAQUE FLUID AND ASSOCIATED IMAGING SYSTEM AND METHOD

PRIORITY

This application is a continuation of copending U.S. Ser. No. 14/478,241, which was filed on Sep. 5, 2014.

FIELD

This application relates to imaging and, more particularly, to the use of nonaqueous radiopaque fluids for radiographic imaging.

BACKGROUND

Various objects, such as mechanical parts (e.g., aircraft parts), are qualitatively tested. Such testing typically focuses on the identification of cracks (e.g., microcracks in welds) or deformations, the occurrence inconsistencies, and/or the evaluation of sizing or fit (e.g., seal fit). Nondestructive testing techniques may be preferred because they do not permanently alter the object under test, thereby allowing the object to be placed into service after testing or allowing further testing by other means.

Radiography is a commonly used nondestructive testing technique that uses high energy (e.g., ionizing) electromagnetic radiation, such as x-rays and gamma rays, to image the internal structure of various objects. However, the quality of radiographic images may be limited by the composition of the object being visualized. For example, there may be little contrast at the interface between a polymeric body and an ambient air-filled void defined by the polymeric body because the radiodensities of the polymer and ambient air may be too similar. Therefore, the resulting radiographic image may depict a poorly defined void structure.

Radiopaque materials have been used to enhance imaging by providing contrast. Traditional radiopaque fluids have been prepared by dissolving or suspending various radiodense compounds in water. However, traditional radiopaque fluids may be incompatible with certain objects (e.g., may be corrosive) and may limit the conditions (temperature and pressure) under which imaging may be performed.

Accordingly, those skilled in the art continue with research and development efforts in the field of imaging.

SUMMARY

In one aspect, the disclosed imaging system includes an imaging device having a field of view and a nonaqueous radiopaque fluid positionable in the field of view.

In another aspect, the disclosed imaging system may include an imaging device having a field of view, an object positioned in the field of view, the object defining a void, and a nonaqueous radiopaque fluid in the void.

In another aspect, the disclosed imaging method may include the steps of (1) contacting an object with a nonaqueous radiopaque fluid and (2) imaging the object, such as with a radiographic imaging device.

In another aspect, the disclosed imaging method may include the steps of (1) preparing a nonaqueous radiopaque fluid; (2) contacting an object with the nonaqueous radiopaque fluid; (3) exposing the object to predetermined testing conditions (temperature and pressure); and (4) imaging the object.

In yet another aspect, the disclosed nonaqueous radiopaque fluid may include a nonaqueous carrier that includes ethylene glycol, propylene glycol and/or hydraulic fluid, and a metal-halide dissolved in the nonaqueous carrier.

Other aspects of the disclosed nonaqueous radiopaque fluid and associated imaging system and method will become apparent from the following detailed description, the accompanying drawings and the appended claims.

BRIEF DESCRIPTION OF THE DRAWINGS

(FIG. 3B);

DETAILED DESCRIPTION

Figure 1:
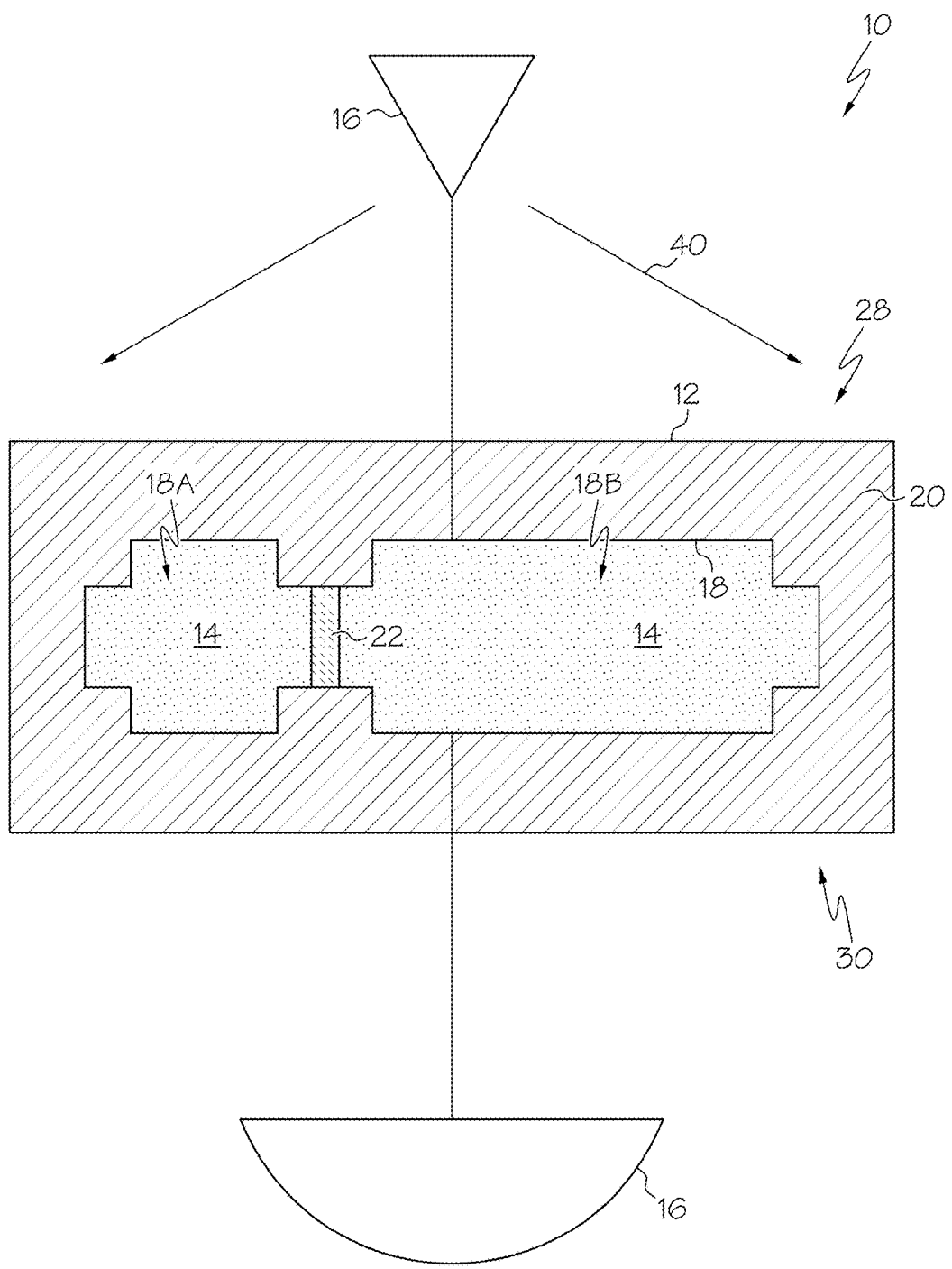
FIG. 1 is a schematic representation of one aspect of the disclosed imaging system.

Referring to FIG. 1, one aspect of the disclosed imaging system, generally designated 10, may include an object 12 under test, a nonaqueous radiopaque fluid 14 and an imaging device 16. The object 12 may define a void 18, such as a crack (e.g., a microcrack), a chamber, a bore, a recess, a depression or the like. The nonaqueous radiopaque fluid 14 may be received in the void 18. For example, the nonaqueous radiopaque fluid 14 may at least partially, if not fully, fill the void 18. Therefore, the nonaqueous radiopaque fluid 14 may enhance contrast when the imaging device 16 images the object 12.

The object 12 may be any article having a body 20 that defines the void 18 for receiving the nonaqueous radiopaque fluid 14 and that is capable of being imaged by the imaging device 16. As one general, non-limiting example, the object 12 may be a mechanical part, such as a mechanical part for an aircraft.

Compositionally, the body 20 of the object 12 may be formed from various materials or a combination of materials, while still being imageable with the imaging device 16. As one non-limiting example, the body 20 of the object 12 may be formed from a metal or metal alloy. As another non-limiting example, the body 20 of the object 12 may be formed from a polymer. As yet another non-limiting example, the body 20 of the object 12 may be formed from a composite, such as a fiber-reinforced (e.g., carbon fiber-reinforced) composite material.

Referring to the specific, non-limiting example shown in FIG. 1, the body 20 of the object 12 may be metallic (e.g., an aluminum alloy) and may define an elongated chamber (void 18). A polymeric seal 22 may be positioned to separate the void 18 into a first chamber 18A and a second chamber 18B. Both the first and second chambers 18A, 18B may be filled with the nonaqueous radiopaque fluid 14. Therefore, the object 12 may include a metallic component (body 20) having a first radiodensity and a non-metallic component (polymeric seal 22) having a second radiodensity. The nonaqueous radiopaque fluid 14 may have a third radiodensity, which may be different (e.g., less) than the first radiodensity, but substantially more than the second radiodensity. During imaging, the nonaqueous radiopaque fluid 14 may provide the contrast necessary to view the polymeric seal 22. At this point, those skilled in the art will appreciate that without the nonaqueous radiopaque fluid 14 the seal 22 may not be viewable due to the similarity in the radiodensities of the polymer forming the seal 22 and the ambient air (rather than nonaqueous radiopaque fluid 14) filling the chambers 18A, 18B.

In one implementation, the nonaqueous radiopaque fluid 14 includes a nonaqueous carrier and a radiodense solute. The solute may be dissolved in the nonaqueous carrier. Any undissolved solute may be removed, such as by centrifuging the nonaqueous carrier/solute mixture and decanting the supernatant liquid, thereby yielding a single-phase solution for use as the nonaqueous radiopaque fluid 14.

The nonaqueous carrier of the disclosed nonaqueous radiopaque fluid 14 may be any nonaqueous compound or mixture of nonaqueous compounds that renders the nonaqueous radiopaque fluid 14 a liquid at the desired imaging temperature and pressure. In one expression, the nonaqueous radiopaque fluid 14 may be a liquid at all temperatures between about −50° C. and at least about 200° C. In another expression, the nonaqueous radiopaque fluid 14 may be a liquid at all temperatures between about −50° C. and at least about 150° C. In another expression, the nonaqueous radiopaque fluid 14 may be a liquid at all temperatures between about −25° C. and at least about 125° C. In yet another expression, the nonaqueous radiopaque fluid 14 may be a liquid at all temperatures between about −65° C. and at least about 120° C.

In one particular formulation, the nonaqueous carrier of the disclosed nonaqueous radiopaque fluid 14 may be (or may include) a glycol. One example of a glycol suitable for use as the nonaqueous carrier of the disclosed nonaqueous radiopaque fluid 14 is ethylene glycol. Another example of a glycol suitable for use as the nonaqueous carrier of the disclosed nonaqueous radiopaque fluid 14 is propylene glycol.

In another particular formulation, the nonaqueous carrier of the disclosed nonaqueous radiopaque fluid 14 may be (or may include) a hydraulic fluid. One example of a hydraulic fluid suitable for use as the nonaqueous carrier of the disclosed nonaqueous radiopaque fluid 14 is RADCOL-UBE® FR282 hydraulic fluid, which is commercially available from Radco Industries, Inc., of LaFox, Ill. Another example of a hydraulic fluid suitable for use as the nonaqueous carrier of the disclosed nonaqueous radiopaque fluid 14 is SKYDROL® hydraulic fluid, which is commercially available from Eastman Chemical Company of Kingsport, Tenn.

The solute of the disclosed nonaqueous radiopaque fluid 14 may be substantially radiodense. The magnitude of the radiodensity of the solute may be dictated by the radiodensity of the object 12 (or the various components of the object 12 in the case of multi-component objects 12). As one example, more radiodensity may be required when the object 12 under test comprises metal or metal alloys, while less radiodensity may be sufficient when the object 12 under test is comprised of polymeric materials.

The radiodensity of the nonaqueous radiopaque fluid 14 may be greater than (or less than) the radiodensity of the material (or radiodensities of the materials) being imaged. When the object under test includes multiple materials having different radiodensities, the radiodensity of the nonaqueous radiopaque fluid 14 may be between the radiodensities of two or more of the materials.

The presence of the solute may render the nonaqueous radiopaque fluid 14 substantially more radiodense than ambient air. As one example, the solute may be selected to yield a nonaqueous radiopaque fluid 14 having a radiodensity of at least about −500 Hounsfield units. As another example, the solute may be selected to yield a nonaqueous radiopaque fluid 14 having a radiodensity of at least about −200 Hounsfield units. As another example, the solute may be selected to yield a nonaqueous radiopaque fluid 14 having a radiodensity of at least about 0 Hounsfield units. As another example, the solute may be selected to yield a nonaqueous radiopaque fluid 14 having a radiodensity of at least about 100 Hounsfield units. As another example, the solute may be selected to yield a nonaqueous radiopaque fluid 14 having a radiodensity of at least about 200 Hounsfield units. As another example, the solute may be selected to yield a nonaqueous radiopaque fluid 14 having a radiodensity of at least about 500 Hounsfield units. As yet another example, the solute may be selected to yield a nonaqueous radiopaque fluid 14 having a radiodensity of at least about 700 Hounsfield units.

In one general realization, the solute of the disclosed nonaqueous radiopaque fluid 14 may be a salt. In one specific realization, the solute of the disclosed nonaqueous radiopaque fluid 14 may be a metal-halide salt. Examples of metal-halides suitable for use as the solute of the disclosed nonaqueous radiopaque fluid 14 include, but are not limited to, zinc iodide ($ZnI_2$), zinc chloride ($ZnCl_2$) and potassium iodide (KI). Without being limited to any particular theory, the use of salts of heavier (by atomic weight) halogens, such as iodine, may render the nonaqueous radiopaque fluid 14 more radiodense than a nonaqueous radiopaque fluid 14 formulated with lighter (by atomic weight) halogens. The use of salts of heavier (by atomic weight) metals may also render the nonaqueous radiopaque fluid 14 more radiodense.

In another implementation, the nonaqueous radiopaque fluid 14 includes radiodense particles suspended in a nonaqueous carrier. The suspension may be prepared by dispersing the particles in the nonaqueous carrier. An optional dispersing agent may be added to the mixture to inhibit settling out of the suspended particles.

As one specific, non-limiting example, the suspension may be prepared by mixing a solute (e.g., a salt, such as a metal-halide salt) with a nonaqueous carrier. However, rather than removing any undissolved solute, the undissolved solute may be kept suspended in the nonaqueous carrier (e.g., by constant agitation).

In yet another implementation, the nonaqueous radiopaque fluid 14 may be a solvent-only composition (no solute or suspended particles may be required to render radiodense the solvent-only nonaqueous radiopaque fluid 14). The solvent-only nonaqueous radiopaque fluid 14 may be a single chemical component composition, though mixtures of solvents may also be used.

In one expression, the solvent-only nonaqueous radiopaque fluid 14 may be a chlorinated solvent. Examples of chlorinated solvents that may be used as the solvent-only nonaqueous radiopaque fluid 14 include, but are not limited to, methylene chloride, chloroform, carbon tetrachloride, chlorobenzene and combinations thereof.

In another expression, the solvent-only nonaqueous radiopaque fluid 14 may be a brominated solvent. Examples of brominated solvents that may be used as the solvent-only nonaqueous radiopaque fluid 14 include, but are not limited to, ethyl bromide, n-propyl bromide, iso-propyl bromide, bromobenzene and combinations thereof.

The imaging device 16 may be any apparatus or system capable of imaging an object positioned in its field of view 40. In one particular manifestation, the imaging device 16 may be a radiographic imaging device. Therefore, the imaging device 16 may include a source 24 of ionizing radiation (e.g., x-rays and/or gamma rays) and a detector 26. For example, the source 24 may be (or may include) an x-ray source and the detector 26 may be (or may include) an x-ray detector. The source 24 may be positioned proximate (at or near) a first side 28 of the object 12 and the detector 26 may be positioned proximate a second side 30 of the object, thereby directing ionizing radiation through the object toward the detector 26. The use of other energy-based imaging technologies, such as ultrasound and other non-visible light-based technologies, is also contemplated.

Figure 2:
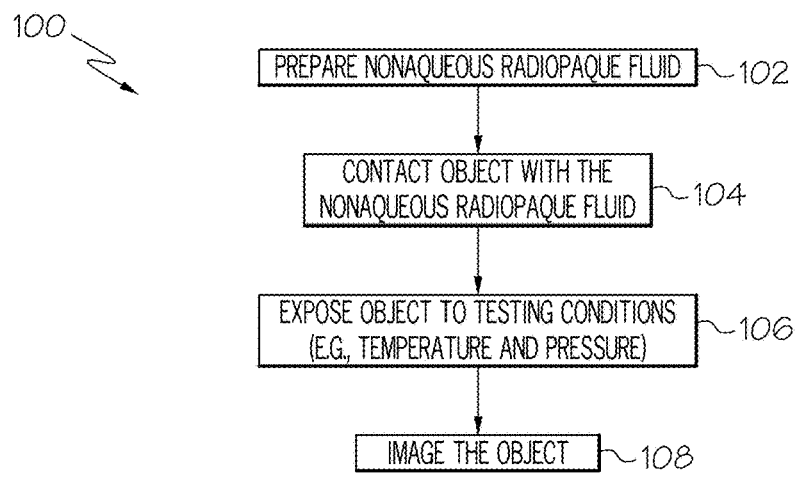
FIG. 2 is a flow diagram depicting one aspect of the disclosed imaging method.

Referring to FIG. 2, also disclosed is an imaging method, which is generally designated 100. The method 100 may be used to evaluate an object, such as for cracks (e.g., microcracks in welds), deformations or other damage, for leakage or failure, and/or for sizing or fit.

At Block 102, a nonaqueous radiopaque fluid may be prepared. In one implementation, the nonaqueous radiopaque fluid may include a nonaqueous carrier and a radiodense solute, such as a metal-halide salt. The radiodense solute may be dissolved, at least partially, in the nonaqueous carrier. In another implementation, the nonaqueous radiopaque fluid may include radiodense particles suspended in a nonaqueous carrier. In yet another implementation, the nonaqueous radiopaque fluid may be a solvent-only composition (e.g., a single chemical component composition).

At Block 104, the object may be contacted with the nonaqueous radiopaque fluid. The object may define one or more voids, such as a crack (e.g., a microcrack), a chamber, a bore, a recess, a depression or the like. Therefore, contacting the object with the nonaqueous radiopaque fluid may include filling (at least partially if not fully) the void with the nonaqueous radiopaque fluid.

At Block 106, the object may optionally be exposed to predetermined testing conditions. As one example, the object may be heated or cooled to the desired testing temperature. As another example, the object may be pressurized or depressurized to the desired testing pressure. As yet another example, the object may be exposed to both the desired testing temperature and the desired testing pressure.

At Block 108, the object may be imaged using an imaging device. For example, the object (at the desired testing conditions and with nonaqueous radiopaque fluid-filled voids) may be subjected to radiographic imaging, wherein x-rays are passed from an x-ray source, through the object, and ultimately, to an x-ray detector.

EXAMPLES

Examples 1-6

Six sample nonaqueous radiopaque fluids were prepared by saturating various nonaqueous carriers with various metal-halide salts. Specifically, an excess quantity of each salt was dissolved in the associated nonaqueous carrier by sonicating the mixture, centrifuging and then decanting the supernatant fluid into a glass test vial such that no visible solid was present. The glass test vials were sealed with metal crimps.

The nonaqueous carriers used were ethylene glycol, propylene glycol and RADCOLUBE® FR282 hydraulic fluid from Radco Industries, Inc., of LaFox, Ill. The salts used were zinc iodide ($ZnI_2$), zinc chloride ($ZnCl_2$) and potassium iodide (KI). The specific formulations are provided in Table 1.

TABLE 1

| Sample | Carrier | Salt |
|---|---|---|
| 1 | Ethylene Glycol | KI |
| 2 | Ethylene Glycol | $ZnI_2$ |
| 3 | Propylene Glycol | KI |
| 4 | Propylene Glycol | $ZnI_2$ |
| 5 | RADCOLUBE ® | $ZnI_2$ |
| 6 | Propylene Glycol | $ZnCl_2$ |

Figure 3A:
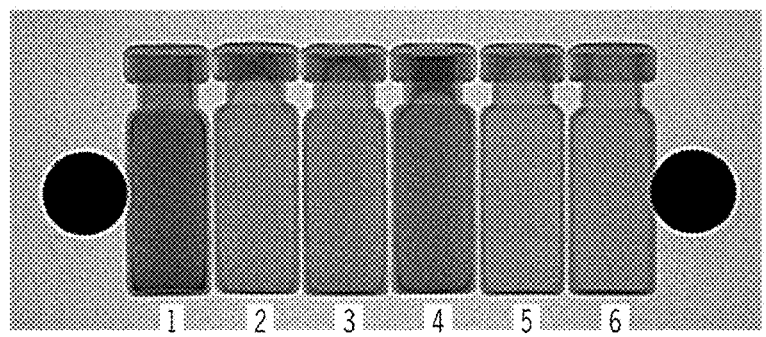
FIGS. 3A and 3B are x-ray images of six vials filled with samples of the disclosed nonaqueous radiopaque fluid, shown at ambient temperature (FIG. 3A) and at −54° C.
Figure 3B:
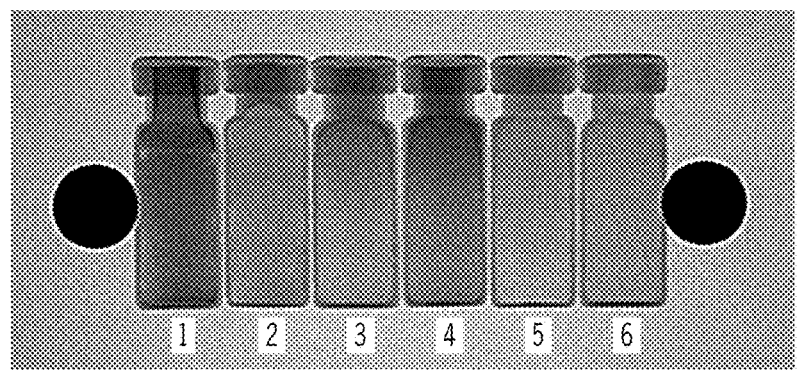

The sample vials were imaged with x-rays. The result is shown in FIG. 3A. Then, the sample vials were stored in a freezer set at −76° C., at which temperature some of the formulations solidified. The sample vials were then transferred to the imaging cabinet and imaged at less than or equal to −54° C. (target temperature for the original test). Initially, some of the radiopaque formulations were in liquid state and some were in solid state. They warmed until all six radiopaque formulations were in a liquid state as they approached ambient temperature. The sample vials were again imaged with x-rays. The result is shown in FIG. 3B. Significantly, there is no discernable difference between the image taken at ambient temperature and the image taken at the coldest temperature (solid and liquid formulations) which was below −54° C.

Examples 7-9

Three sample nonaqueous radiopaque fluids were prepared by saturating SKYDROL® hydraulic fluid with various metal-halide salts, particularly zinc iodide ($ZnI_2$), zinc chloride ($ZnCl_2$) and potassium iodide (KI). The specific formulations are provided in Table 2.

TABLE 2

| Sample | Carrier | Salt |
|---|---|---|
| 7 | SKYDROL ® | $ZnI_2$ |
| 8 | SKYDROL ® | $ZnCl_2$ |
| 9 | SKYDROL ® | KI |

Figure 4:
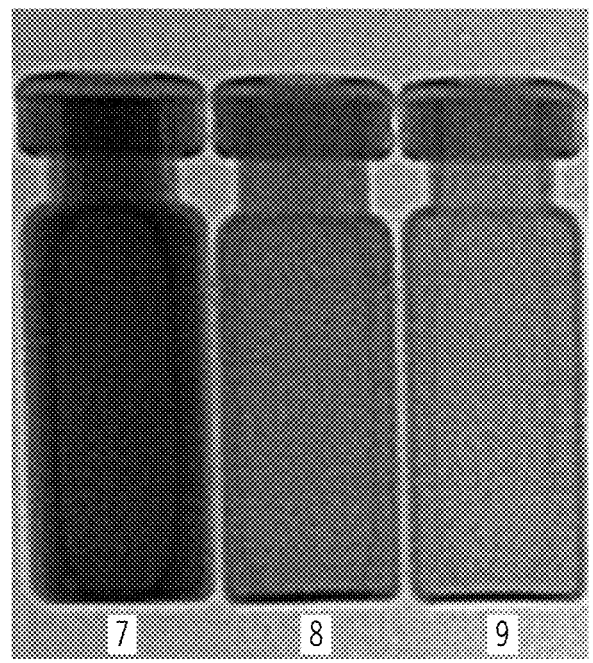
FIG. 4 is an x-ray image of three vials filled with samples of the disclosed nonaqueous radiopaque fluid.

An excess quantity of each salt was dissolved in the SKYDROL® hydraulic fluid by sonicating the mixture, centrifuging and then decanting the supernatant fluid into a glass test vial such that no visible solid was present. The glass test vials were sealed with metal crimps and imaged with x-rays (at ambient temperature). The result is shown in FIG. 4. Without being limited to any particular theory, it is believed that the greater radiodensity of Sample 7 relative to Samples 8 and 9 is due to the greater solubility of zinc iodide in SKYDROL® hydraulic fluid.

Accordingly, the disclosed imaging system 10 and imaging method 100 may employ a nonaqueous radiopaque fluid to facilitate imaging various objects. Advantageously, the use of nonaqueous radiopaque fluids (as compared to traditional water-based fluids) may reduce the risk of corrosion and other material incompatibility issues, and may broaden (or at least shift) the pressure and temperature ranges under which imaging may be performed. Furthermore, because nonaqueous radiopaque fluids do not undergo the extensive expansion that aqueous formulations do during freezing, using solid phase (frozen) nonaqueous radiopaque fluids for very cold temperatures is a possibility.

Figure 5:
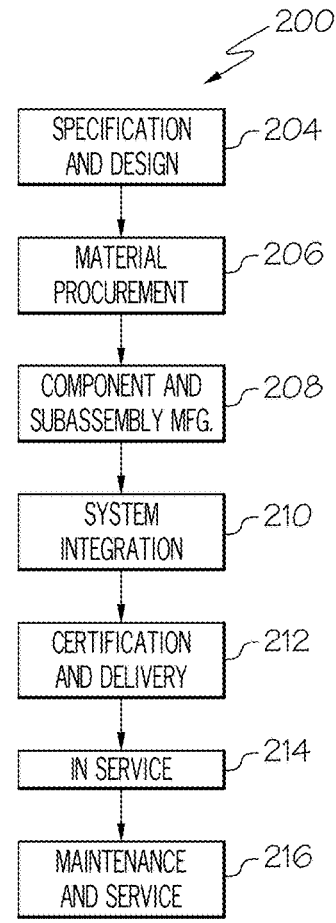
FIG. 5 is a flow diagram of an aircraft manufacturing and service methodology.
Figure 6:
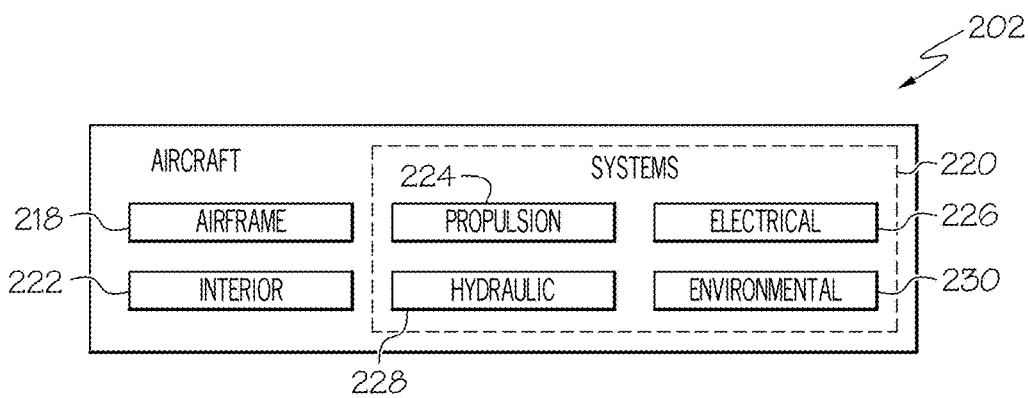
FIG. 6 is a block diagram of an aircraft.

Examples of the disclosure may be described in the context of an aircraft manufacturing and service method 200, as shown in FIG. 5, and an aircraft 202, as shown in FIG. 6. During pre-production, the aircraft manufacturing and service method 200 may include specification and design 204 of the aircraft 202 and material procurement 206. During production, component/subassembly manufacturing 208 and system integration 210 of the aircraft 202 takes place. Thereafter, the aircraft 202 may go through certification and delivery 212 in order to be placed in service 214. While in service by a customer, the aircraft 202 is scheduled for routine maintenance and service 216, which may also include modification, reconfiguration, refurbishment and the like.

Each of the processes of method 200 may be performed or carried out by a system integrator, a third party, and/or an operator (e.g., a customer). For the purposes of this description, a system integrator may include without limitation any number of aircraft manufacturers and major-system subcontractors; a third party may include without limitation any number of venders, subcontractors, and suppliers; and an operator may be an airline, leasing company, military entity, service organization, and so on.

As shown in FIG. 6, the aircraft 202 produced by example method 200 may include an airframe 218 with a plurality of systems 220 and an interior 222. Examples of the plurality of systems 220 may include one or more of a propulsion system 224, an electrical system 226, a hydraulic system 228, and an environmental system 230. Any number of other systems may be included.

The disclosed nonaqueous radiopaque fluid and associated imaging system and method may be employed during any one or more of the stages of the aircraft manufacturing and service method 200. For example, components or subassemblies corresponding to component/subassembly manufacturing 208, system integration 210, and or maintenance and service 216 may be fabricated or manufactured using the disclosed nonaqueous radiopaque fluid and associated imaging system and method. Also, one or more apparatus examples, method examples, or a combination thereof may be utilized during component/subassembly manufacturing 208 and/or system integration 210, for example, by substantially expediting assembly of or reducing the cost of an aircraft 202, such as the airframe 218 and/or the interior 222. Similarly, one or more of system examples, method examples, or a combination thereof may be utilized while the aircraft 202 is in service, for example and without limitation, to maintenance and service 216.

The disclosed system and method are described in the context of an aircraft; however, one of ordinary skill in the art will readily recognize that the disclosed service system may be utilized for a variety of different components for a variety of different types of vehicles. For example, implementations of the aspects described herein may be implemented in any type of vehicle including, e.g., helicopters, passenger ships, automobiles and the like.

Although various aspects of the disclosed nonaqueous radiopaque fluid and associated imaging system and method have been shown and described, modifications may occur to those skilled in the art upon reading the specification. The present application includes such modifications and is limited only by the scope of the claims.

What is claimed is:

1. An imaging system comprising:
   an imaging device having a field of view; and
   a nonaqueous radiopaque fluid positionable in said field of view, said nonaqueous radiopaque fluid having a radiodensity that is between that of a metallic portion and a non-metallic portion of an object to be imaged by said imaging device.

2. The imaging system of claim 1 wherein said imaging device comprises a source of ionizing radiation and a detector.

3. The imaging system of claim 1 wherein said nonaqueous radiopaque fluid is a liquid at temperatures ranging from at least −50° C. to at least 150° C.

4. The imaging system of claim 1 wherein said nonaqueous radiopaque fluid comprises a nonaqueous carrier and a solute.

5. The imaging system of claim 4 wherein said nonaqueous carrier comprises at least one of ethylene glycol and propylene glycol.

6. The imaging system of claim 4 wherein said nonaqueous carrier comprises a hydraulic fluid.

7. The imaging system of claim 4 wherein said solute comprises a metal-halide.

8. The imaging system of claim 4 wherein said solute comprises at least one of zinc iodide, zinc chloride and potassium iodide.

9. The imaging system of claim 4 wherein said nonaqueous radiopaque fluid comprises a single-phase.

10. The imaging system of claim 1 wherein said nonaqueous radiopaque fluid comprises particles in suspension.

11. The imaging system of claim 1 wherein said nonaqueous radiopaque fluid is a solvent-only composition.

12. A method for imaging a mechanical part defining a void and comprising a metallic component having a first radiodensity and a non-metallic component having a second radiodensity, said method comprising:
   contacting said mechanical part with a nonaqueous radiopaque fluid such that said nonaqueous radiopaque fluid is received in said void, wherein said nonaqueous radiopaque fluid has a third radiodensity, said third radiodensity being less than said first radiodensity and substantially greater than said second radiodensity; and
   imaging said mechanical part while said nonaqueous radiopaque fluid is received in said void.

13. The method of claim 12 wherein said contacting step comprises filling said void with said nonaqueous radiopaque fluid.

14. The method of claim 12 wherein said imaging step comprises passing ionizing radiation through said object.

15. The method of claim 12 further comprising exposing said object to predetermined testing conditions prior to said imaging step.

16. The method of claim 12 wherein said nonaqueous radiopaque fluid comprises a nonaqueous carrier and a solute at least partially dissolved in said nonaqueous carrier.

17. The method of claim 12 wherein said nonaqueous radiopaque fluid comprises a metal-halide.

18. The method of claim 12 wherein said nonaqueous radiopaque fluid comprises at least one of zinc iodide, zinc chloride and potassium iodide.

19. The method of claim 12 wherein said nonaqueous radiopaque fluid comprises a single-phase.

20. The method of claim 12 wherein said nonaqueous radiopaque fluid is a liquid at temperatures ranging from at least −50° C. to at least 150° C.

* * * * *